(12) United States Patent
Chin et al.

(10) Patent No.: US 10,349,957 B2
(45) Date of Patent: Jul. 16, 2019

(54) SYSTEMS AND METHODS FOR TRAVERSING A SITE OF OBSTRUCTION

(71) Applicant: Cruzar Medsystems, Inc., Braintree, MA (US)

(72) Inventors: Albert K. Chin, Palo Alto, CA (US); Thomas Kramer, San Carlos, CA (US); Michael Glennon, Norwell, MA (US)

(73) Assignee: Cruzar Medsystems, Inc., Braintree, MA (US)

( * ) Notice: Subject to any disclaimer, the term of this patent is extended or adjusted under 35 U.S.C. 154(b) by 265 days.

(21) Appl. No.: 15/347,118

(22) Filed: Nov. 9, 2016

(65) Prior Publication Data
US 2018/0125510 A1 May 10, 2018

(51) Int. Cl.
*A61B 17/22* (2006.01)
*A61B 17/3207* (2006.01)

(52) U.S. Cl.
CPC .......... *A61B 17/22* (2013.01); *A61B 17/3207* (2013.01); *A61B 2017/22038* (2013.01);
(Continued)

(58) Field of Classification Search
CPC .......... A61B 17/22; A61B 2017/22038; A61B 2017/22047; A61B 2017/22048;
(Continued)

(56) References Cited

U.S. PATENT DOCUMENTS 3,669,099 A  6/1972 Silverman
3,831,587 A  8/1974 Boyd
(Continued)

FOREIGN PATENT DOCUMENTS

EP  0227583  7/1987
EP  0359489  3/1990
(Continued)

OTHER PUBLICATIONS

International Search Report in International Application No. PCT/US2017/059972 dated Feb. 28, 2018.
(Continued)

*Primary Examiner* — Ryan J. Severson
(74) *Attorney, Agent, or Firm* — Greenberg Traurig, LLP; Chinh H. Pham

(57) ABSTRACT

Systems for providing access across a site of obstruction and methods for manufacturing and using such systems are provided. Such systems may include a cannula having a lumen, an everting member coupled to the cannula, and a push assembly having a pathway. The push assembly may be slidably disposed within the lumen of the cannula and connected to a proximal end of the everting member to move the everting member from an inverted position inside the cannula to an everted position outside the cannula. The systems may also include a tube having a passageway, the tube slidably disposed within the pathway of the push assembly and extending through a proximal end of the push assembly into the pathway of the push assembly to selectively move from a first position inside the push assembly to a second position outside the push assembly.

11 Claims, 3 Drawing Sheets

(52) U.S. Cl.
CPC ............... *A61B 2017/22044* (2013.01); *A61B 2017/22049* (2013.01); *A61B 2017/22075* (2013.01); *A61B 2017/22094* (2013.01)

(58) Field of Classification Search
CPC ........... A61B 2017/22049; A61B 2017/22051; A61B 2017/22054; A61B 2017/22065; A61B 2017/22067; A61B 2017/22069; A61B 2017/22072; A61B 2017/22094; A61B 2017/22095; A61M 25/0194; A61M 25/09; A61M 25/09041; A61M 2025/0197; A61M 2025/09125; A61M 2025/1065
See application file for complete search history.

(56) References Cited

U.S. PATENT DOCUMENTS

| | | | |
|---|---|---|---|
| 3,911,927 A | 10/1975 | Rich et al. | |
| 4,043,345 A | 8/1977 | Kramann et al. | |
| 4,109,659 A | 8/1978 | Sheridan | |
| 4,243,040 A | 1/1981 | Beecher | |
| 4,254,774 A | 3/1981 | Boretos | |
| 4,493,711 A | 1/1985 | Chin et al. | |
| 4,630,609 A | 12/1986 | Chin | |
| 4,863,440 A | 9/1989 | Chin | |
| 4,871,358 A | 10/1989 | Gold | |
| 4,960,411 A | 7/1990 | Buchbinder et al. | |
| 5,171,305 A | 12/1992 | Shickling et al. | |
| 5,295,960 A | 3/1994 | Aliahmad et al. | |
| 5,458,573 A | 10/1995 | Summers | |
| 6,767,338 B2 | 7/2004 | Hawk et al. | |
| 6,979,290 B2 | 12/2005 | Mourlas et al. | |
| 7,144,407 B1 | 12/2006 | Lasersohn | |
| 7,494,485 B2 | 2/2009 | Beck | |
| 7,794,447 B2 | 9/2010 | Dann et al. | |
| 8,343,170 B2 * | 1/2013 | Massicotte | A61B 17/22032 606/127 |
| 8,491,519 B2 | 7/2013 | Chin | |
| 8,529,581 B2 * | 9/2013 | Massicotte | A61B 17/22032 606/127 |
| 8,556,851 B2 * | 10/2013 | Hirszowicz | A61M 25/0119 604/96.01 |
| 8,657,849 B2 * | 2/2014 | Parker | A61B 17/221 606/200 |
| 8,827,951 B2 * | 9/2014 | Besser | A61B 17/22032 604/97.02 |
| 8,894,680 B2 * | 11/2014 | Hirszowicz | A61M 25/0119 606/194 |
| 8,926,559 B2 | 1/2015 | Chin | |
| 9,326,790 B2 | 5/2016 | Chin et al. | |
| 9,439,662 B2 * | 9/2016 | Hirszowicz | A61B 17/22032 |
| 9,463,035 B1 * | 10/2016 | Greenhalgh | A61B 17/221 |
| 9,782,570 B2 * | 10/2017 | Hirszowicz | A61M 25/0119 |
| 9,795,408 B2 * | 10/2017 | Chin | A61B 17/3403 |
| 2002/0120226 A1 | 8/2002 | Beck | |
| 2003/0144629 A1 | 7/2003 | Hawk et al. | |
| 2005/0049718 A1 | 3/2005 | Dann et al. | |
| 2007/0083158 A1 | 4/2007 | Hirszowicz et al. | |
| 2009/0204069 A1 * | 8/2009 | Hirszowicz | A61M 25/0119 604/103.04 |
| 2011/0172584 A1 | 7/2011 | Chin | |
| 2011/0213469 A1 | 9/2011 | Chin et al. | |
| 2012/0302996 A1 | 11/2012 | Barash | |
| 2014/0343593 A1 | 11/2014 | Chin et al. | |
| 2015/0066068 A1 * | 3/2015 | Hirszowicz | A61B 17/22032 606/194 |
| 2015/0088187 A1 | 3/2015 | Chin et al. | |
| 2015/0126966 A1 * | 5/2015 | Hirszowicz | A61M 25/0119 604/509 |
| 2015/0142045 A1 | 5/2015 | Bacich | |
| 2018/0125510 A1 * | 5/2018 | Chin | A61B 17/22 |

FOREIGN PATENT DOCUMENTS

| | | |
|---|---|---|
| GB | 1482873 | 8/1977 |
| JP | S50-149171 A | 11/1975 |
| JP | S58-500694 A | 5/1983 |
| JP | S59-501149 A | 7/1984 |
| WO | 82/03989 A1 | 11/1982 |
| WO | 84/00113 A1 | 1/1984 |
| WO | 2000/007657 | 2/2000 |
| WO | 2001/083017 | 11/2001 |
| WO | 2003/084584 | 10/2003 |
| WO | 2011/088381 | 7/2011 |
| WO | 2012/048142 | 4/2012 |

OTHER PUBLICATIONS

European Search Report issued in European Application No. 15178491.5, dated Mar. 18, 2016.
Extended European Search Report issued in European Application No. 11831621.5, dated Feb. 26, 2014.
International Search Report issued in PCT Application PCT/US11/55149, dated Jan. 23, 2012.
Office Action issued for U.S. Appl. No. 13/267,657, dated Oct. 9, 2012.
Office Action issued for U.S. Appl. No. 14/073,270, dated Jan. 16, 2015.
Partial European Search Report issued in EP 15178491.5, dated Dec. 21, 2015.

* cited by examiner

SYSTEMS AND METHODS FOR TRAVERSING A SITE OF OBSTRUCTION

BACKGROUND

Obstructions within pipes, tubes, body cavities, and vessels can often inhibit access through the pipes, tubes, body cavities, and vessels. For example, disuse, low flow, slow flow, contaminants, unwanted chemical reactions, and/or obstructive material can narrow or block pipes, tubes, or drains in a household, commercial, laboratory, or industrial setting. Similarly, for example, atherosclerosis and other circulatory diseases occur when the arteries become narrowed or blocked. Plaque formation within the arteries can cause occlusive lesions or other obstructions on the artery wall. Similarly, clots, thrombus, stenosis, or tortuosity in a vessel can also act to inhibit access or movement through the vessel. Such an obstruction can also cause health problems by impeding movement of fluid through the vessel. For example, if the vessel is a blood vessel, the obstruction may impede blood flow.

In addition, the ability of the obstruction to block the vessel can also create issues during surgery. For example, during a surgical procedure (e.g., angioplasty, stent placement, or other procedures within a cavity or vessel) a surgeon may require access, along the vessel, to a site distal to the obstruction. In other situations, a surgeon may wish to deliver a stent, catheter, or other device to the site of obstruction so that fluid, surgical devices, and/or other material can move across the obstruction. However, it can often be difficult to pass a catheter or other devices across the area of obstruction in the presence of an obstruction in the vessel. Repeated attempts and increased advancement force can be dangerous, as such acts may result in vessel perforation or laceration.

Accordingly, it would be desirable to have a system that can provide access across an obstruction in a pipe, tube, body cavity, or vessel in order to provide easier passage therethrough while minimizing potential damage to the walls of the pipe, tube, body cavity, or vessel.

SUMMARY OF THE INVENTION

In some embodiments, a system for providing access across a site of obstruction is provided. The system includes a cannula having a proximal end, a distal end, and a lumen extending therebetween. The system also includes an everting member having a first end coupled to the distal end of the cannula and a second end. The system also includes a push assembly having a pathway along its entire length, the push assembly being slidably disposed across the proximal end of the cannula into the lumen of the cannula and being connected at its distal end to the second end of the everting member, such that advancement of the push assembly along the lumen of the cannula moves the everting member from an inverted position within the lumen of the cannula to an everted position outside the cannula. The system also includes a tube having a passageway and being coaxially disposed within the pathway of the push assembly, the tube being slidably movable across a proximal end of the push assembly.

In some embodiments, a method for traversing a site of obstruction is provided. The method includes a step of advancing a guidewire through a tube and an everting member inverted into a lumen of a cannula. The method also includes a step of pressurizing the everting member to grip the guidewire. The method also includes a step of everting the everting member from the cannula to distally advance the guidewire gripped by the everting member. The method also includes a step of depressurizing the everting member to release the guidewire. The method also includes a step of advancing the tube to a distal end of the guidewire. The method also includes a step of pressurizing the everting member to grip the tube. The method also includes a step of inverting the everting member into the lumen. The method also includes a step of depressurizing the everting member to release the tube. The method also includes a step of advancing the cannula to a distal end of the guidewire.

DETAILED DESCRIPTION

In accordance with various embodiments of the present invention, systems and methods are provided for providing access across an obstruction, such as an obstruction observed in connection with a complete or partial blockage within a vessel caused by, for instance, a clot, stenosis, or tortuosity within a blood vessel. The systems and methods described below may also, in some instances, be used to navigate past difficult regions in vessels, including arteries, veins, ureters, urethra, Fallopian tubes, pancreatic ducts, nasal sinuses, or any luminal structures or cavities in the body as well as pipes, ducts, tubes, or other passages in an industrial, commercial, household, or laboratory setting.

Figure 1:
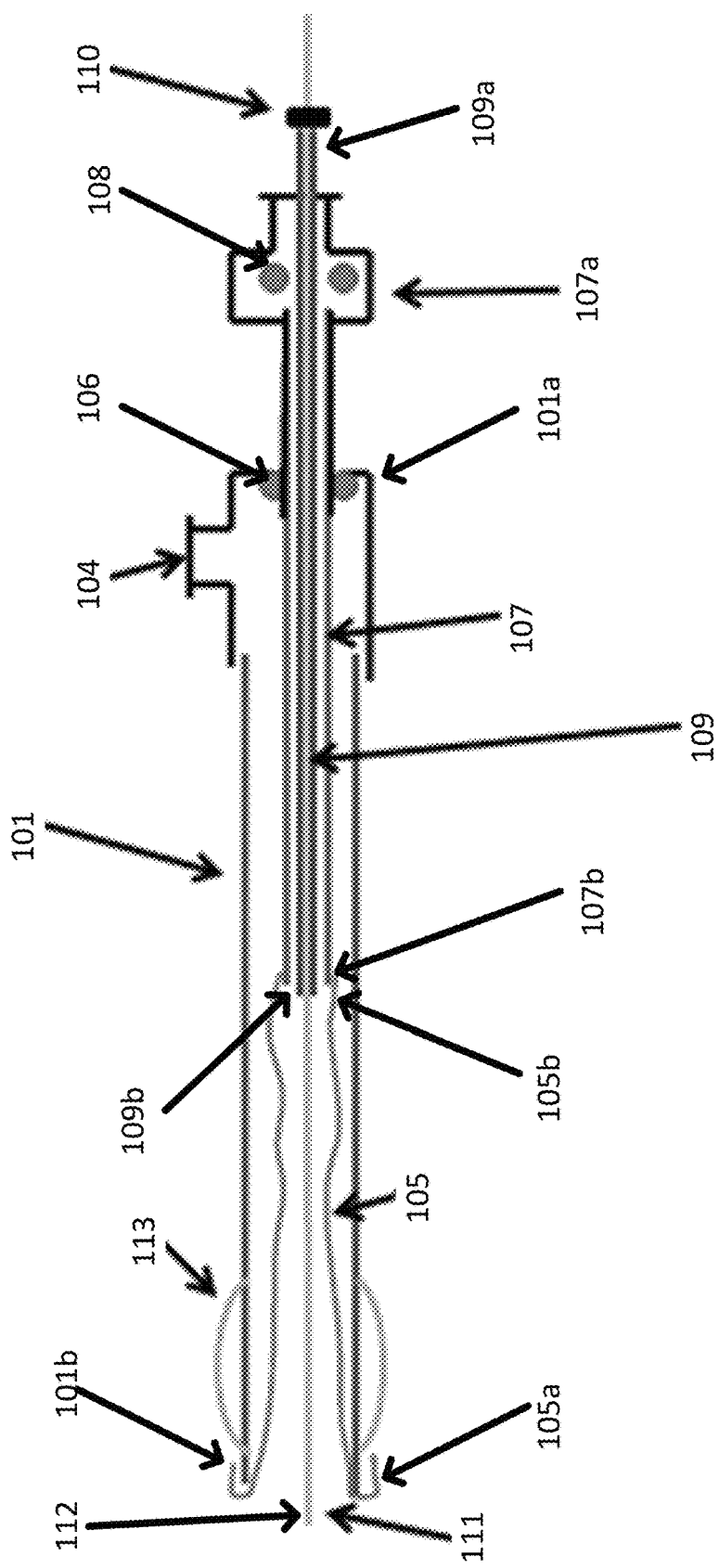
FIG. 1 illustrates a system for providing access across an area of obstruction in accordance with various embodiments.

Referring now to FIG. 1, a system 100 for providing access across a site of an obstruction is provided. The system 100, in some embodiments, includes a cannula 101 defining a lumen extending between a proximal end 101a and a distal end 101b thereof for insertion into the obstructed pipeline, vessel, artery, tube, pipe, or other passageway and navigation to the site of obstruction. As illustrated in FIG. 1, the cannula 101 can be substantially tubular in shape. It should be noted, however, that while described as being tubular in shape, the cannula 101 may have any other shape desired depending on the particular application, as the shape of the cannula 101 may aid in the navigation of the cannula 101 to provide access across a site of obstruction.

In some embodiments, the cannula 101 may be sufficiently flexible so that it can navigate through a tortuous path in a vessel, tube, or pipe. Additionally or alternatively, the cannula 101 may be sufficiently rigid so that it does not bend or fold in the presence of a proximal force being applied for advancing cannula 101 through the vessel, tube, or pipe.

The cannula 101 may also have any desired length, depending upon the application, so long as cannula 101 can be advanced through a vessel to the site of obstruction. For example, in some embodiments, cannula 101 may be relatively long, e.g. a long catheter, so that it can be advanced through a long or tortuous vessel to a site of obstruction. In another embodiment, cannula 101 may be a relatively short sleeve that can be delivered across the obstruction. The cannula 101 may also have any diameter sufficient to allow the cannula 101 to fit within a vessel, depending upon the application and the size of the vessel. In an embodiment, the diameter of the cannula 101 may remain substantially constant throughout. If desired, the diameter of the cannula 101 may vary, as necessary, along the length of the cannula 101.

In some embodiments, the cannula 101 may further include a coating on an outer surface to reduce friction between the cannula 101 and the vessel wall upon insertion into the vessel. In some embodiments, the coating may cover the entire outer surface of the cannula 101. In an alternative embodiment, the coating may be located only at a distal end 101*b* of the cannula 101. However, it will be apparent in view of this disclosure that the coating may be placed onto the outer surface in other manners as well. Likewise, the cannula 101 may include a coating on an inner surface to reduce friction during eversion of an everting member 105. In some embodiments, the inner coating may cover the entire inner surface of the cannula 101. In some embodiments, the coating may be located only at the distal end 101*b* of the cannula 101. It will be apparent in view of this disclosure that the coating may be placed onto the inner surface in other manners as well. The distal end 101*b* of the cannula 101, in some embodiments, can be coupled to the everting member 105.

In some embodiments, fluid can be introduced or evacuated from the lumen of the cannula 101 via a port 104 formed in or otherwise coupled in fluid communication with the lumen of the cannula 101 for permitting pressurization and depressurization of the everting member 105. For example, in some embodiments, fluids such as, for example, air, saline, any other suitable fluid, or combinations thereof can be introduced or evacuated from the lumen of the cannula 101 via the port 104.

The port 104, in accordance with various embodiments, can be configured for delivering or removing one or more fluids (e.g., air, a gas, a saline solution, water, or any other suitable fluid) to the lumen for pressurizing and depressurizing the everting member 105. In some embodiments, the port 104 can also be in fluid communication with an anchoring member 113 for pressurizing and depressurizing the anchoring member 113. In some embodiments, the anchoring member 113 can include a valve or other resealable mechanism to permit independent pressurization and depressurization of the anchoring member 113 and the everting member 105. In some embodiments, a second port (not shown) can be included to provide independent pressurization and depressurization of the anchoring member 113.

The port 104, in some embodiments, may be a tube, pipe, or other passage, for example, through which fluid can flow. In some embodiments, port 104 may be permanently or detachably coupled to the cannula 101. In some embodiments, port 104 may be integral with the cannula 101. To that end, the cannula 101 and the port 104 may be manufactured as a single unit.

In some embodiments, the port 104 can include a connector integrated with the port 104 to facilitate coupling of the port 104 to an inflation mechanism (not shown), that can direct fluid into and out of the lumen and the everting member 105 through port 104. The inflation mechanism may be a pump (e.g. a manual or automatic pump), syringe, or other device that can pressurize and/or depressurize (e.g., inflate or deflate) the everting member 105 during use. In some embodiments, the port 104 may be utilized as a pressurization port to inflate the everting member 105 by fluidly connecting the everting member 105 to the inflation mechanism. It will be apparent in view of this disclosure that, in some embodiments, other locations and configurations for the inflation port are possible as long as fluids can enter with a sufficient force to pressurize and depressurize the everting member 105. In some embodiments, the port 104 may be sealable to provide a fluid seal between the lumen of the cannula 101 and the ambient space.

The system 100, in some embodiments, includes an everting member 105 for gripping and advancing a guidewire 111 when pressurized. In some embodiments, the everting member 105 can also enter and/or expand, via pressurization within the channel, a pre-existing or previously formed channel through the site of obstruction. In some embodiments, the everting member 105 can be coupled at a first end 105*a* to the distal end of the cannula 101 and coupled at a second end 105*b* to a distal end 107*b* of a push assembly 107.

In some embodiments, the everting member 105 can include any flexible or deformable, substantially fluid impermeable material capable of being pressurized and/or depressurized by introduction of a fluid. For example, in some embodiments, the everting member can be made of one or more of PET, nylon, nylon elastomers, polyurethane, other suitable flexible or deformable materials, or combinations thereof. In some embodiments, the everting member 105, although flexible, can be substantially inelastic to withstand relatively high pressurization levels and to provide more precise control over eversion and inversion distances. As described with greater detail below, the everting member 105, in some embodiments, can be configured to grasp (i.e., by friction) and advance the guidewire 111 in response to advancement of the push assembly 107. In some embodiments, such configurations permit the user to exercise more precise control over deployment of the everting member 105 and guidewire 111. In some embodiments, the proximal end of the everting member 105 may be connected to a distal end 107*b* of the push assembly 107.

The push assembly 107, in some embodiments, can be slidable within the cannula 101 to allow a user to manually (or by a mechanical application of force) advance or retract everting member 105. In some embodiments, the push assembly 107 can include a pathway extending therethrough and can be disposed within the lumen of the cannula. In some embodiments, the push assembly 107 can be a catheter, tube, pipe, or any other structure having a pathway extending therethrough and being sufficiently rigid to deliver an eversion or inversion force to the everting member when the push assembly 107 is slid by a user relative to the cannula 101. In some embodiments, the push assembly 107 may be constructed as a single integral piece or, in some embodiments, can be constructed from multiple pieces.

In some embodiments, the second end 105*b* of the everting member 105 can be coupled to the distal end 107*b* of the push assembly 107 to permit the push assembly 107 to advance or retract (evert or invert) the everting member 105. In some embodiments, the push assembly 107 can be coaxially disposed across and through the proximal end 101*a* of the cannula 101 to form a slip fit with the lumen of the cannula 101. Thus movement of the push assembly 107 is permitted in a longitudinal direction within the cannula 101. In some embodiments, the push assembly 107 may be longer than, shorter than, or equal in length to the everting member 105. The proximal end 107*a* of the push assembly 107 can, in some embodiments, protrude proximally out of the cannula 101. In some embodiments, the proximal end 107*a* may be rigid to enable longitudinal displacement of the push assembly 107 as the user or a drive mechanism pushes on the proximal end 107*a*. In some embodiments, a sliding O-ring seal 106 (also known as a Tuohy-Borst seal) may be provided on the fitting at the proximal end of cannula 101 to form a seal between proximal end 107*a* and inner walls of cannula 101. Such fitting may be a Y-connector having an inflation port and the Tuohy-Borst seal 106. The proximal end 107a, in some embodiments, may be constructed of metal such as stainless steel, or a reinforced plastic catheter section that does not collapse within the sliding O-ring seal 106. In some embodiments, the push assembly 107 may be slightly longer than the length of everting member 105, and the proximal end 107a of the push assembly 107 may be connected to a second Tuohy-Borst seal 108 to enable instruments or other tubes or catheters (e.g., tube 109) to be passed through the proximal end 107a. In some embodiments, the second Tuohy-Borst seal 108 may be provided to enable passage of the tube 109 through the cannula 101 during traversal of the site of obstruction.

In some embodiments, the push assembly 107 may be configured to limit the extent of eversion and re-inversion of the everting member 105. By way of a non-limiting example, in connection with embodiments, eversion may be limited such that only the guidewire 111 and the everting member 105 extend through the lesion, and not the push assembly 107 connected to the proximal end of the everting member 105. To that end, a bushing (not shown) may be used to couple the everting member 105 to the cannula 101. As everting member 105 fully everts, the distal end 107b of the push assembly 107 can travel in distal direction until it reaches the bushing, which will act as an eversion stop to prevent push assembly 107 from exiting cannula 101.

Pulling back on the proximal end 107a with a partially pressurized or depressurized everting member 105 may cause the everting member 105 to re-invert. In some embodiments, re-inversion may be limited to prevent tear or detachment of the everting member 105 from the cannula 101 due to undue traction exerted on the everting member 105. In some embodiments, the O-ring seal 106 in the proximal end of cannula 101 can act to limit re-inversion of the everting member 105. As the push assembly 107 is retracted through the Tuohy-Borst seal 106, the push assembly 107 can include a stop member (not shown) for contacting the O-ring seal 106 at full re-inversion of the everting member 105, thus limiting unwanted forces on everting member 105. It should of course be noted that other methods may be used to limit the extent of eversion and re-inversion.

In some embodiments, to provide a non-collapsible element selectively interposable between the everting member 105 and the guidewire 111, a tube 109 can be coaxially disposed within the pathway of the push assembly 107 and slidably movable across and through the proximal end 107a of the push assembly 107. In some embodiments, the tube 109 can include, for example, a rigid or otherwise non-collapsing tube (e.g., a microcatheter) having a passageway extending therethrough. In some embodiments, the tube 109 can form a sliding fit within the pathway of the push assembly 107. In some embodiments, the tube 109 can have a length substantially similar to or longer than an overall length of the cannula 101, the push assembly 107, and the everting member 105 when the everting member is in the everted position. In some embodiments, the tube can be constructed of metals, polymers, stainless steel, polytetrafluoroethylene (PTFE), polyimide, PEEK, nylon, polyethylene, Nitinol, titanium, blended materials, or combinations thereof. In some embodiments, the tube 109 can be composed of a single layer of material or multiple layers of material. In some embodiments, a layer of metal reinforcement may be added to the tube 109 to render it non-collapsing. The reinforcement may be a stainless steel or Nitinol wire braid or coil that is integrated into the structure of the tube 109. In some embodiments, a hub 110 can be bonded onto or integrally formed with a proximal end 109a of the microcatheter, to allow manipulation of the tube 109 relative to the system 100. In some embodiments, the hub 110 can include a fluid seal that can slide along the guidewire 111 when the guidewire 111 is extending through the passageway and can maintain a fluid seal (e.g., a hemostatic seal) between the tube 109 and the guidewire 111. In some embodiments, a colored marker may be present near the proximal end 109a of the tube 109. In some embodiments, this marker may be aligned with the proximal end 107a of the push assembly 107, to indicate proper positioning of the tube 109 within the system 100 prior to use.

In some embodiments, a guidewire 111 can be introduced through the passageway of the tube 109 for guiding placement of the system 100 and for providing penetration of the obstruction. The guidewire 111, in some embodiments, can be any suitable guidewire 111 for extending through the passageway of the tube 109. In some embodiments, the guidewire 111 can be constructed, for example, from one or more of gold, Nitinol, platinum, stainless steel, nickel, titanium, tungsten, alloys thereof, or combinations thereof. In some embodiments, the guidewire 111 can include one or more coatings such as, for example, hydrophilic coatings, anti-thrombogenic coatings, hydrophobic coatings, silicone coatings, or tetrafluoroethylene (TFE) coatings. More generally, the guidewire 111 can be any suitable material or construction for penetrating and/or recanalizing a site of obstruction as described with greater detail below. In some embodiments, the guidewire 111 can include a distal tip 112 for contacting and penetrating the obstruction to be traversed.

In order to fix the system 100 in place proximate the site of obstruction, an anchoring member 113 can be included in some embodiments. The anchoring member 113 can include any flexible or deformable, substantially fluid impermeable material capable of being pressurized and/or depressurized by introduction of a fluid. For example, in some embodiments, the anchoring member can be made of one or more of latex, rubber, PET, nylon, nylon elastomers, polyurethane, other suitable flexible materials, or combinations thereof. In some embodiments, the anchoring member 113 can be flexible and either elastic or inelastic so long as the anchoring member can withstand pressurization without bursting. In general, the anchoring member 113 can be any pressurizable member capable of fixing the system 100 in place within the pipe, tube, vessel, passage, etc. during traversal of the site of obstruction.

In some embodiments, the anchoring member 113 can be pressurized via port 104. In some embodiments, the system 100 can further include a valve or other flow control mechanism (not shown) to permit independent pressurization and depressurization of the anchoring member 113 and the everting member 105. In some embodiments, the system can include a second port (not shown) for independently pressurizing or depressurizing the anchoring member 113.

Referring now to FIGS. 2A-2F, the systems and devices of the present disclosure may, in some embodiments, be used to traverse and/or open a site of obstruction. In some embodiments, the site of obstruction can be completely clogged or occluded with no passage therethrough. In some embodiments, the obstruction can be comprised of a relatively hard material (e.g., calcified deposits in a pipe or a "hard cap" in a blood vessel or artery). In some embodiments, the systems and methods described herein may be used to traverse such obstructions. In general, a guidewire 111 may be advanced distally from the cannula 101 into the obstruction by eversion of the everting member 105. In some embodiments, the everting member 105 is not sufficiently long to advance the guidewire 111 through the entire obstruction. In such embodiments, the everting member 105 can be re-inverted without displacement of the guidewire 111 for subsequent re-eversion and further advancement of the guidewire 111. Thus, the system 100 can advantageously permit traversal of the entire obstruction without a need to reposition and re-align the system 100 after each eversion.

Figure 2A:
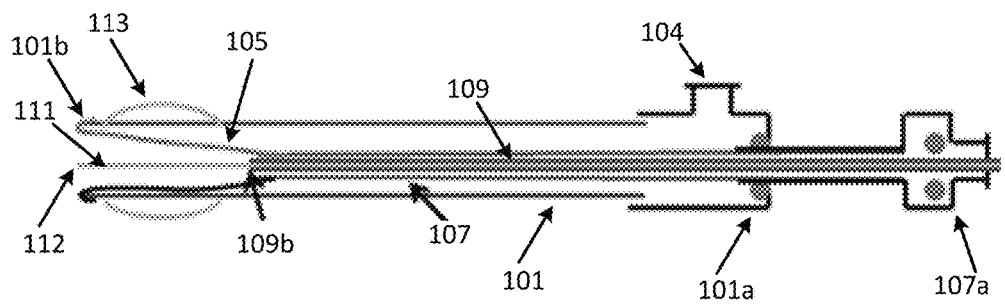
FIGS. 2A-2F illustrate a sequence of steps for using the system of FIG. 1 in accordance with various embodiments.

In use, as shown in FIG. 2A, the system 100 can initially be positioned with the everting member 105 in an inverted position within the lumen of the cannula 101 wherein the push assembly 107 can be substantially retracted. Additionally, the distal end 109b of the tube 109 can be longitudinally positioned substantially coincident with the distal end 107b of the push assembly 107 and the guidewire 111 can be positioned so that a distal tip 111b of the guidewire 111 is longitudinally positioned substantially coincident with the distal end 101b of the cannula 101.

Figure 2B:
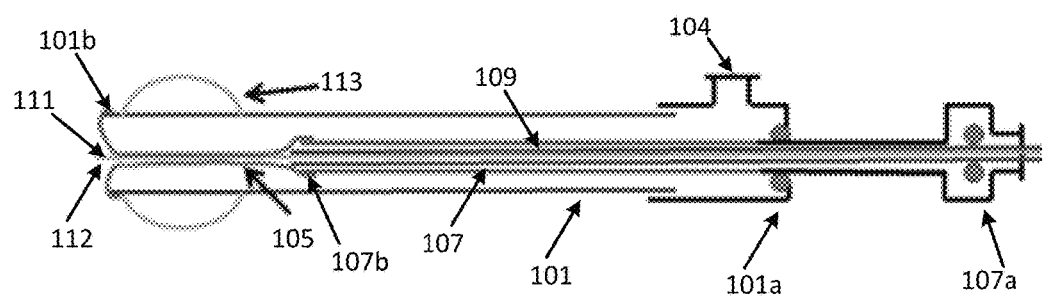

Referring now to FIG. 2B, upon placement of the cannula 101 proximate to the obstruction, the lumen may be pressurized, thereby pressurizing the everting member 105 and causing the everting member 105 to collapse onto the guidewire 111 to securely grip the guidewire 111. In some embodiments, the anchoring member 113 can also be pressurized to fix the cannula 101 in place. As shown in FIG. 2B, the guidewire 111 can be loaded into the pathway of the push assembly 107 and through the everting member 105. Upon pressurization of the everting member 105, substantially the entire length of the everting member 105 may collapse onto the guidewire 111 to securely grip the guidewire 111. In some embodiments, the O-ring seal of the fluid seal 110 on the proximal end of the tube 109 may also be closed onto guidewire 111.

Figure 2C:
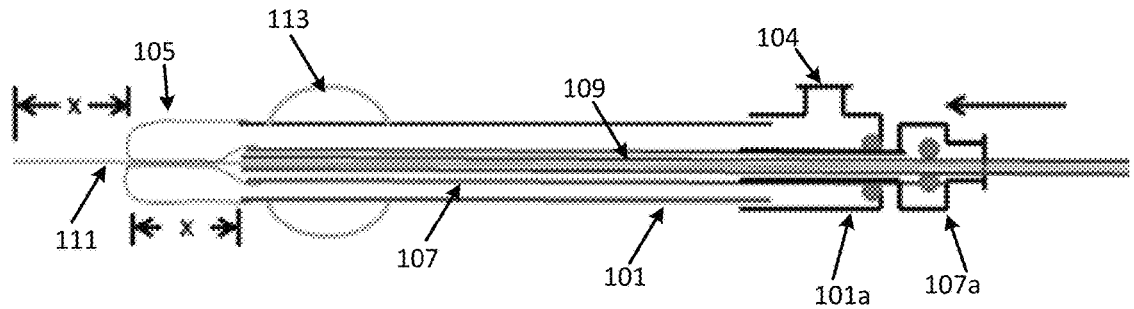

Referring now to FIG. 2C, in some embodiments, the everting member 105 can then be everted by sliding the push assembly 107 distally relative to the cannula 101 to drive the tip 112 of the guidewire 111 into the obstruction. More particularly, when the push assembly 107 is advanced forward to evert the everting member 105, the everting member 105 can advance the tip 112 of the guidewire 111 into the obstruction, while providing a supporting force to enable the guidewire 111 to pierce the cap. In some embodiments, the everting member 105 may push the guidewire 111 forward a distance equal to the distance of push assembly advancement. It should be noted that, in some embodiments, since the everting member 105 advances in a toroidal, double walled configuration, the everting member 105 can advance a distance that is one-half the distance of push assembly 107 advancement. In this manner, guidewire 111 may advance ahead of the leading front of the everting member 105 to penetrate the obstruction. In some embodiments, the everting member 105 may be everted and inverted sequentially to cyclically pulse the guidewire 111 into the obstruction to create an opening into previously impenetrable obstructions.

In operation, the guidewire 111 may be centered inside cannula 101 and may be centered within the pipe, tube, vessel, artery, etc. by the pressurized anchoring member 113. Moreover, the everting member 105 may stabilize the guidewire 111 in such centered position when the everting member 105 is pressurized as shown in FIG. 2B. Advancement of the push assembly 107 may drive distal tip 112 of guidewire 111 into the center of the obstruction, to reopen the obstruction.

In some embodiments, the push assembly 107 may be cyclically advanced and retracted a short distance; e.g. 5-10 mm at a time, to serially drive a guidewire 111 with higher rigidity into the obstruction. In some embodiments, the cannula 101 may be depressurized and the guidewire 111 pulled back, so that upon re-pressurization of cannula 101, only the everting member 105, without the guidewire 111, is advanced through the occlusion. Everting member-only advancement may be performed in situations in which advancement of the guidewire tip preceding the balloon may be dangerous; for example, if vessel curvature or the presence of a bifurcation or branch increases the potential for guidewire perforation.

Once a channel is initiated in the obstruction, if the guidewire 111 was able to traverse the entire obstruction, the guidewire 111 can be removed and everting member 105 can be everted into the channel created in the occlusion. If necessary, guidewires of sequentially increasing size may be used to enlarge the channel before everting member 105 may be everted through the channel.

Figure 2D:
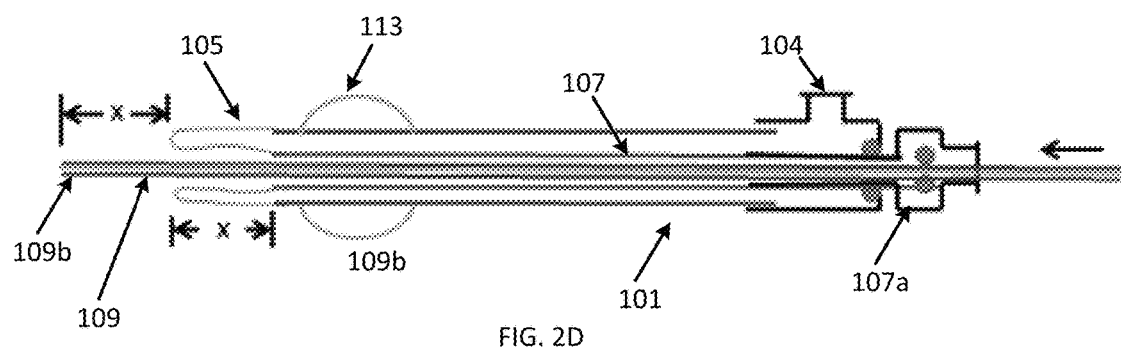
Figure 2E:
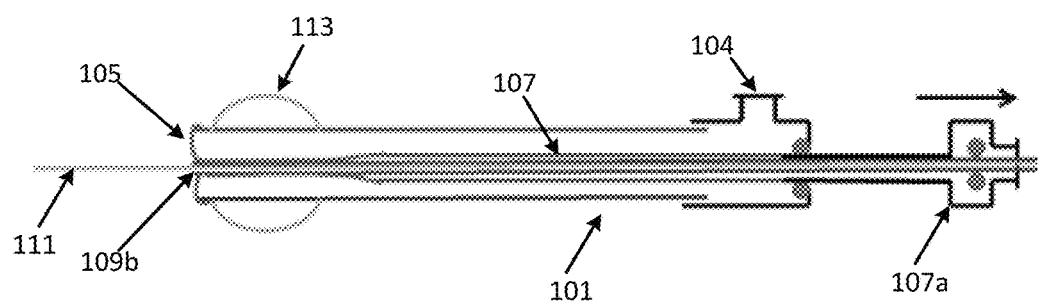
Figure 2F:
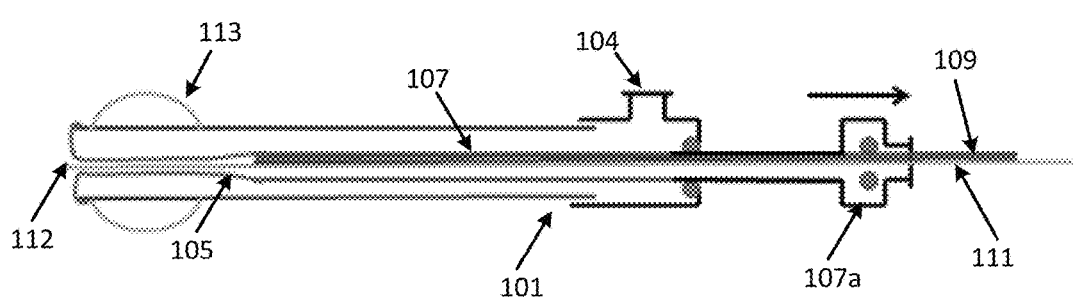

Referring now to FIGS. 2D-2F, if the guidewire 111 is only able to partially traverse the obstruction, the system 100 can advantageously be manipulated to re-invert the everting member 105 without displacement of the guidewire from within the partially formed channel. In such embodiments, as shown in FIG. 2D, with the everting member 105 in the fully everted position, the lumen and everting member 105 can be depressurized and the tube 109 can be advanced relative to the push assembly 107 over the stationary guidewire 111 so as to be interposed between the guidewire 111 and the depressurized everting member 105.

As shown in FIG. 2E, the lumen and everting member 105 can be re-pressurized to collapse onto the tube 109 to securely grip the tube 109. Because the tube 109 is configured to be non-collapsible at operating pressure, the tube 109 remains slidable relative to the stationary guidewire 109. Thus, once the everting member 105 is securely gripping the tube 109, the push assembly 107 can be retracted to re-invert the everting member 105 without retracting the guidewire 111. Instead, the everting member 105 grips the tube 109, which slides proximally, along with the everting member 105, relative to the guidewire 111 during the re-inversion.

In some embodiments, as shown in FIG. 2F, the everting member 105 can then be depressurized again and the distal end 109b of the tube 109 can be slid back into substantial longitudinal alignment with the distal end of the push assembly as described above with reference to FIG. 2A. In some embodiments, as shown in FIG. 2F, while the everting member 105 is depressurized, the cannula 101 can be advanced such that the distal end 101b of the cannula is aligned with the tip 112 of the guidewire 111. The guidewire 111 can then be further advanced into the obstruction by repeating the steps described above with reference to FIGS. 2A-2F until the obstruction has been traversed by the guidewire 111.

Alternatively, in some embodiments, where the guidewire 111 is rigid enough and/or the obstruction is soft enough, the cannula 101 does not need to be advanced after re-inversion of the everting member 105 and, instead, the everting member 105 can simply be repressurized to continue advancing the guidewire 111 from the original position of the cannula 101.

Although described in portions hereof as providing access across a site of obstruction within a vessel within a body, the invention can provide access across other sites of obstruction as well. For example, the invention can be used to provide access across an obstruction in a cavity or other type of opening. Furthermore, the invention is not limited to use within the medical field. The sleeve can, for instance, be delivered across an obstruction in a pipeline, drain, tube, or other type of passage, etc. Additionally, since the balloon may be designed to seek the path of least resistance, as described above, the invention may be used to seek out hidden or unknown pathways through various sites of obstruction. In other embodiments, the invention may be equipped with an object or device to be delivered across a site of obstruction. In such an embodiment, the device may be situated on the distal end 101b of cannula 101, a distal end of everting member 105, or on a distal end 109b of the tube 109 so that as the everting member 105 extends through the site of obstruction, the object is delivered to an area distal to the site of obstruction.

While the invention has been described in connection with specific embodiments, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A system for providing access across a site of obstruction comprising:
    a cannula having a proximal end, a distal end, and a lumen extending therebetween;
    an everting member being situated within the lumen, having a first end coupled to the distal end of the cannula and a second end, and being inflatable within the cannula;
    a push assembly, positioned within the lumen, having a pathway along its entire length, the push assembly being slidably disposed across the proximal end of the cannula into the lumen of the cannula and being connected at its distal end to the second end of the everting member, such that advancement of the push assembly along the lumen of the cannula moves the everting member from an inverted position within the lumen of the cannula to an everted position outside the cannula;
    an anchoring member circumferentially placed about an outer surface of the cannula and in the fluid communication with the lumen; and
    a tube having a passageway and being coaxially disposed within the pathway of the push assembly, the tube being slidably movable across a proximal end of the push assembly,
    wherein the lumen provides a path along which pressurizing fluid can be introduced and evacuated from the cannula, such that in the presence of pressurizing fluid, the anchoring member inflates while the everting member inflates, and in the absence of pressurizing fluid, the anchoring member deflates while the everting member deflates.

2. The system of claim 1, further comprising a bushing disposed at the distal end of the cannula to couple the first end of the everting member to the distal end of the cannula.

3. The system of claim 1, wherein the anchoring member being in the fluid communication with the lumen of the cannula and being expandable from a deflated position to an inflated position anchors the cannula near a site of obstruction when the lumen is pressurized to an anchoring pressure sufficient to anchor the cannula in proximity to the site of obstruction.

4. The system of claim 1, further comprising a sealing member disposed between walls of the lumen and the push assembly to seal the lumen.

5. The system of claim 1, further comprising a sealing member disposed between walls of the pathway and the tube to seal the pathway.

6. The system of claim 1, wherein the passageway is configured to receive a guidewire therethrough.

7. A method for traversing a site of obstruction comprising:
    advancing a guidewire through a tube and an everting member inverted into a lumen of a cannula;
    pressurizing the everting member to grip the guidewire;
    everting the everting member from the cannula to distally advance the guidewire gripped by the everting member;
    depressurizing the everting member to release the guidewire;
    advancing the tube to a distal end of the guidewire;
    pressurizing the everting member to grip the tube;
    inverting the everting member into the lumen;
    depressurizing the everting member to release the tube; and
    advancing the cannula to a distal end of the guidewire.

8. The method of claim 7, wherein, in the advancing step, the cannula further comprises an anchoring member coupled to the cannula, the anchoring member being in fluid communication with the lumen and being expandable from a depressurized position to a pressurized position to anchor the cannula near the site of obstruction when the everting member is pressurized.

9. The method of claim 7, further comprising:
    re-pressurizing the everting member to grip the guidewire;
    re-everting the everting member from the cannula to further distally advance the guidewire gripped by the everting member.

10. The method of claim 9, wherein the step of everting the everting member further comprises advancing a push assembly connected to a proximal end of the everting member to move the everting member from an inverted position inside the cannula to an everted position outside the cannula.

11. The method of claim 10:
    the push assembly slidably disposed within the lumen of the cannula; and
    the tube slidably disposed within a pathway of the push assembly and extending through a proximal end of the push assembly into the pathway of the push assembly to selectively move from a first position inside the push assembly to a second position outside the push assembly.

* * * * *